United States Patent
Roundhill

(10) Patent No.: US 11,109,839 B2
(45) Date of Patent: ***Sep. 7, 2021

(54) IMAGING SYSTEMS AND METHODS FOR POSITIONING A 3D ULTRASOUND VOLUME IN A DESIRED ORIENTATION

(71) Applicant: KONINKLIJKE PHILIPS N.V., Eindhoven (NL)

(72) Inventor: David Nigel Roundhill, Woodinville, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/292,883

(22) Filed: Mar. 5, 2019

(65) Prior Publication Data

US 2019/0192118 A1  Jun. 27, 2019

Related U.S. Application Data

(63) Continuation of application No. 15/304,150, filed as application No. PCT/IB2015/053409 on May 9, 2015, now Pat. No. 10,376,241.

(60) Provisional application No. 61/990,740, filed on May 9, 2014.

(51) Int. Cl.
*A61B 8/08* (2006.01)
*A61B 8/00* (2006.01)
*G06T 19/20* (2011.01)

(52) U.S. Cl.
CPC ............ *A61B 8/483* (2013.01); *A61B 8/0866* (2013.01); *A61B 8/4245* (2013.01); *A61B 8/466* (2013.01); *A61B 8/5215* (2013.01); *G06T 19/20* (2013.01); *G06T 2219/2004* (2013.01)

(58) Field of Classification Search
CPC ......... G06T 15/00–87; G06T 19/00–20; G06T 19/20; G06T 2219/2004; A61B 8/483; A61B 8/0866; A61B 8/4245; A61B 8/466; A61B 8/5215; G16H 50/20
See application file for complete search history.

(56) References Cited

U.S. PATENT DOCUMENTS

| | | |
|---|---|---|
| 5,315,999 A | 5/1994 | Kinicki et al. |
| 5,997,479 A | 12/1999 | Savord et al. |
| 6,013,032 A | 1/2000 | Savord |
| 6,368,281 B1 | 4/2002 | Solomon et al. |
| 6,416,476 B1 | 7/2002 | Ogasawara et al. |
| 6,419,633 B1 | 7/2002 | Robinson et al. |

(Continued)

OTHER PUBLICATIONS

Elnokrashy, Ahmed, et al., "Multipass GPU surface rendering in 4D ulrasound", Biomedical Engineering Conference (CIBEC), 2012 Cairo International IEEE, 2012.

*Primary Examiner* — Daniel F Hajnik

(57) ABSTRACT

Methods and systems are provided for displaying a 3D ultrasound image volume in a desired view orientation. A 3D ultrasound image can be acquired of an anatomical feature in a patient. The actual orientation of the anatomical feature can be determined in space. The 3D ultrasound image including the anatomical feature can be displayed such that the anatomical feature is positioned in a selected orientation that is different than the actual orientation, and in relation to a lighting model for generating lighting and shadowing on the anatomical feature.

17 Claims, 3 Drawing Sheets

(56) References Cited

U.S. PATENT DOCUMENTS

| | | | |
|---|---|---|---|
| 2006/0052695 A1* | 3/2006 | Adam | A61N 7/00 |
| | | | 600/437 |
| 2008/0155468 A1 | 6/2008 | Rosander et al. | |
| 2009/0124906 A1 | 5/2009 | Caluser | |
| 2011/0125016 A1 | 5/2011 | Lazebnik et al. | |
| 2012/0245465 A1 | 9/2012 | Hansegard et al. | |
| 2013/0072797 A1 | 3/2013 | Lee | |
| 2013/0150719 A1* | 6/2013 | Orderud | G06T 15/08 |
| | | | 600/443 |
| 2014/0081141 A1 | 3/2014 | Nishihara et al. | |
| 2014/0139526 A1* | 5/2014 | Kim | G06T 7/0012 |
| | | | 345/424 |
| 2014/0205168 A1 | 7/2014 | Kim | |
| 2014/0219548 A1 | 8/2014 | Wels et al. | |
| 2014/0253544 A1* | 9/2014 | Arakita | A61B 6/032 |
| | | | 345/419 |
| 2014/0328526 A1* | 11/2014 | Wahrenberg | A61B 8/5207 |
| | | | 382/131 |
| 2015/0051489 A1 | 2/2015 | Caluser et al. | |
| 2015/0100787 A1* | 4/2015 | Westin | G06F 21/602 |
| | | | 713/168 |
| 2015/0116323 A1 | 4/2015 | Buckton et al. | |
| 2015/0257738 A1* | 9/2015 | Kim | A61B 8/468 |
| | | | 600/440 |

\* cited by examiner

IMAGING SYSTEMS AND METHODS FOR POSITIONING A 3D ULTRASOUND VOLUME IN A DESIRED ORIENTATION

CROSS-REFERENCE TO RELATED APPLICATIONS

This application is a continuation of U.S. patent application Ser. No. 15/304,150, filed on Oct. 14, 2016, which is the U.S. National Phase Application under 35 U.S.C. § 371 of International Application No. PCT/IB2015/053409, filed on May 9, 2015, which claims the benefit of U.S. Provisional Application No. 61/990,740, filed on May 9, 2014, the disclosure of which is hereby incorporated by reference herein.

This invention relates to medical diagnostic ultrasound systems and, in particular, to imaging systems and methods for displaying a 3D ultrasound image in a desired view orientation.

With the advent of high resolution 3D renderings of ultrasound data, diagnostic ultrasound applications have seen continued improvement with better 3D imaging and increased capabilities to identify tissue features not as easily recognized in traditional 2D scanning procedures. Nevertheless, the simplicity and efficiency for certain 3D ultrasound applications still need improvement. For example, an increasingly important expectation is being placed on routine obstetrical ultrasound examinations by mothers that want 3D rendering of their baby's face. Attempting to generate this image is necessary from a business standpoint for many clinicians whose patients will go elsewhere if the service is not available. Unfortunately, obtaining good quality 3D renderings of a baby's face can be a frustrating and time consuming exercise that also takes away from time that can be spent on ultrasound diagnostic scans having more clinical value. Thus, there is need to arrive at the desired imaging result as quickly as possible and save time for clinically relevant screening of the fetus for various potential anomalies. More generally, there is a need for better methods to display a 3D ultrasound image in a desired view orientation according to settings that are optimal for viewing for a certain ultrasound application. The present invention provides this and more.

In accordance with the principles of the present invention, methods and systems are provided for displaying a 3D ultrasound image in a desired view orientation. As described further herein, the present invention can include acquiring 3D ultrasound image data comprising an anatomical feature in a patient. In addition, an actual orientation of the anatomical feature can be determined in relation to a transducer probe or other point of interest. For instance, a fetus can be imaged using a 3D ultrasound system and the orientation of the fetus's face can be determined. The present invention further includes displaying the 3D ultrasound image data as a rendering of the anatomical feature such that the anatomical feature is positioned in a selected orientation that is different than the actual orientation. In addition, the anatomical features being rendered can be positioned in spatial relation to a lighting model such that lighting and shadowing regions on the anatomical features are displayed to a user, and in some embodiments, according to a stored setting on an ultrasound system.

Figure 1:
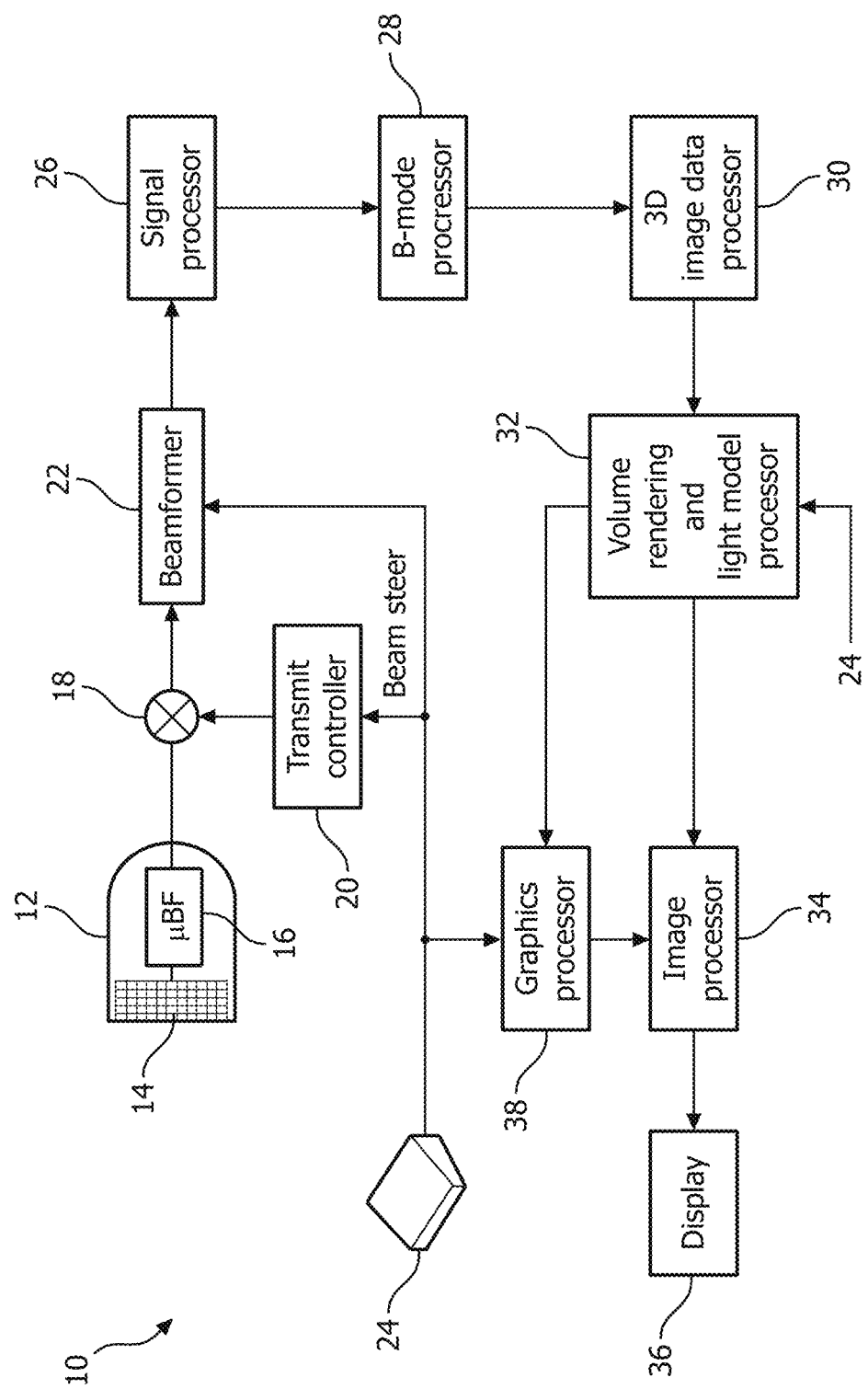
FIG. 1 illustrates in block diagram form the use of three dimensional ultrasonic imaging to guide or monitor ablation in an embodiment of the present invention.

Referring to FIG. 1, an ultrasound imaging system 10 constructed in accordance with the principles of the present invention is shown in block diagram form. In the ultrasonic diagnostic imaging system of FIG. 1, an ultrasound probe 12 includes a transducer array 14 for transmitting ultrasonic waves and receiving echo information. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the probe 12 which controls transmission and reception of signals by the transducer elements in the array. In this example, the microbeamformer is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. In some embodiments, the probe 12 can contain all of the components necessary for outputting a video signal that can be simply displayed by an external display. For example, a system may not include a main beamformer 22, and instead beamforming may be completed in the probe 12, and the probe can also include the signal processor 26, the B mode processor 28, and other electronics for processing ultrasound signals.

As shown, the transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. In this embodiment, the partially beamformed signals produced by the microbeamformer 16 are coupled to a main beamformer 22 where partially beamformed signals from individual patches of transducer elements are combined into a fully beamformed signal. Groups of adjacent transducer elements referred to as "patches" or "subarrays" are integrally operated by a microbeamformer (µBF) in the probe 12. Suitable two dimensional arrays are described in, e.g., U.S. Pat. No. 6,419,633 (Robinson et al.) and in U.S. Pat. No. 6,368,281 (Solomon et al.) Microbeamformers are described, e.g., in U.S. Pat. No. 5,997,479 (Savord et al.) and U.S. Pat. No. 6,013,032 (Savord), all of which are incorporated herein by reference.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of anatomical features, such as a baby's face in the mother. The signals produced by the B mode processor are coupled to a 3D image data processor 30, which is configured to generate 3D image datasets that can be rendered and processed by the volume rendering and light model processor 32. As will be described further herein, the volume rendering and light model processor 32 can render an imaged anatomical feature such that the anatomical feature is positioned in a selected orientation that is different than an actual orientation of the feature in relation to the transducer probe 12. The volume rendering and light model processor 32 also can position the orientation of the anatomical feature in spatial relation to a lighting model such that lighting and shadowing regions on the anatomical feature are displayed according to a stored setting on an ultrasound system. As such, the user interface or control panel 24 can be operated by a user to predefine the stored setting on the system and thereby generate the user's desired view of the anatomical feature along with an optimal lighting arrangement for generating renderings of the anatomical feature, such as a baby's face.

The methods of the present invention are carried out using ultrasound systems as described herein. For example, the ultrasound systems can operate to perform any of the following steps: acquire 3D ultrasound image data comprising an anatomical feature in a patient; determine an actual orientation of the anatomical feature in space; and/or display the 3D ultrasound image data as a rendering comprising the anatomical feature such that the anatomical feature is positioned (1) in a selected orientation that is different than the actual orientation and (2) in spatial relation to a lighting model such that lighting and shadowing regions on the anatomical feature are displayed according to a stored setting on an ultrasound system.

Figure 2:
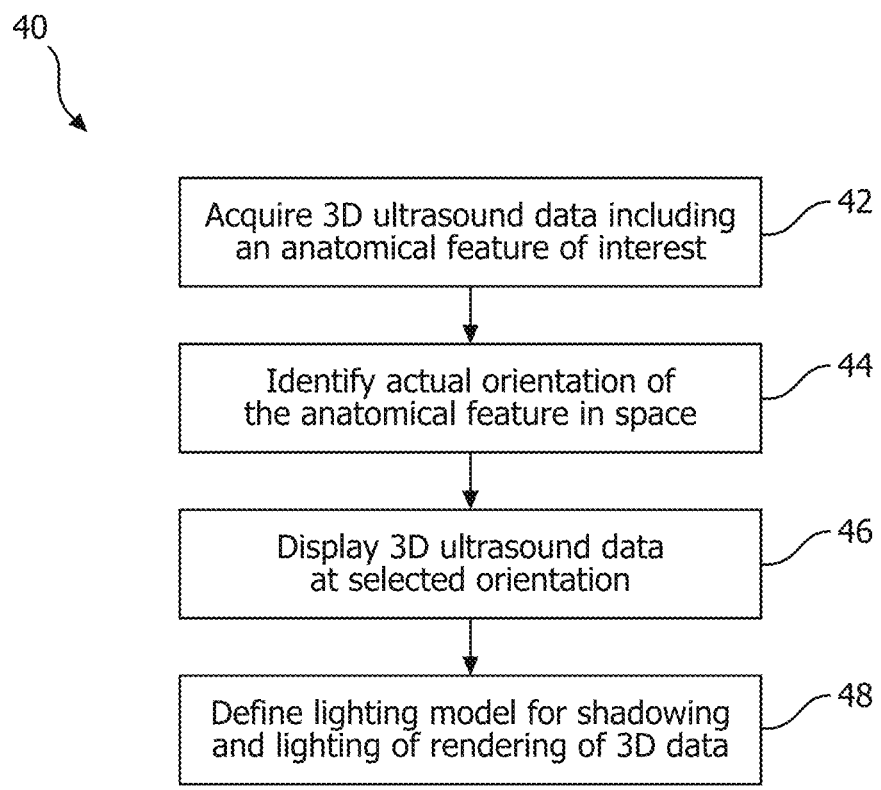
FIG. 2 illustrates a workflow in accordance with the present invention for displaying 3D ultrasound data a selected orientation.

FIG. 2 is a flow chart showing the workflow 40 of an implementation of the present invention. This workflow 40 begins with a step 42 that includes acquiring 3D ultrasound image data that includes at least a portion of an anatomical feature of interest. For example, as described further herein, a 3D ultrasound imaging system can be used to collect images of a fetus in a mother. The anatomical features of interest might include, but are not limited to, the nose, chin, eyes and/or skull of the fetus. In some embodiments, an anatomical feature of interest might include at least a portion of a patient's organ, such as a heart, kidney or liver.

In step 44, an ultrasound system can be used to process the 3D ultrasound data such that an actual orientation of the anatomical feature (e.g., a baby's face) can be determined and, optionally, displayed to a user on a screen. This step includes known techniques for performing 3D ultrasound imaging in which the probe transmits and receives echo data from the patient to show a 2D or 3D image of the patient's anatomy on a display. In some embodiments, automated detection of the orientation of the anatomical feature can be accomplished using structural modeling and anatomical landmark identification. In certain embodiments, the present invention can include identifying the actual orientation by applying structural models to define a surface orientation of the anatomical feature and/or identifying anatomical landmarks in the anatomical feature.

In one aspect, the method for determining the actual orientation of the anatomical feature (e.g., a fetus' face) follows the methods described in Cuignet et al., 2013 IEEE Symposium on Biomedical Imaging, pages 768-771, which is incorporated herein by reference. The method of determining actual orientation can include, for example, identifying anatomical features of a fetus that are echogenic independently of the probe position: the skull, the midsagittal plane and the orbits of the eyes. The skull can be detected and segmented using a shape model and a template deformation algorithm. An initial anatomical frame of reference can thus be defined. Then, the detection of both the midsagittal plane and orbits of the eyes allows to remove orientation ambiguities and eventually to refine this frame of reference.

Figure 3:
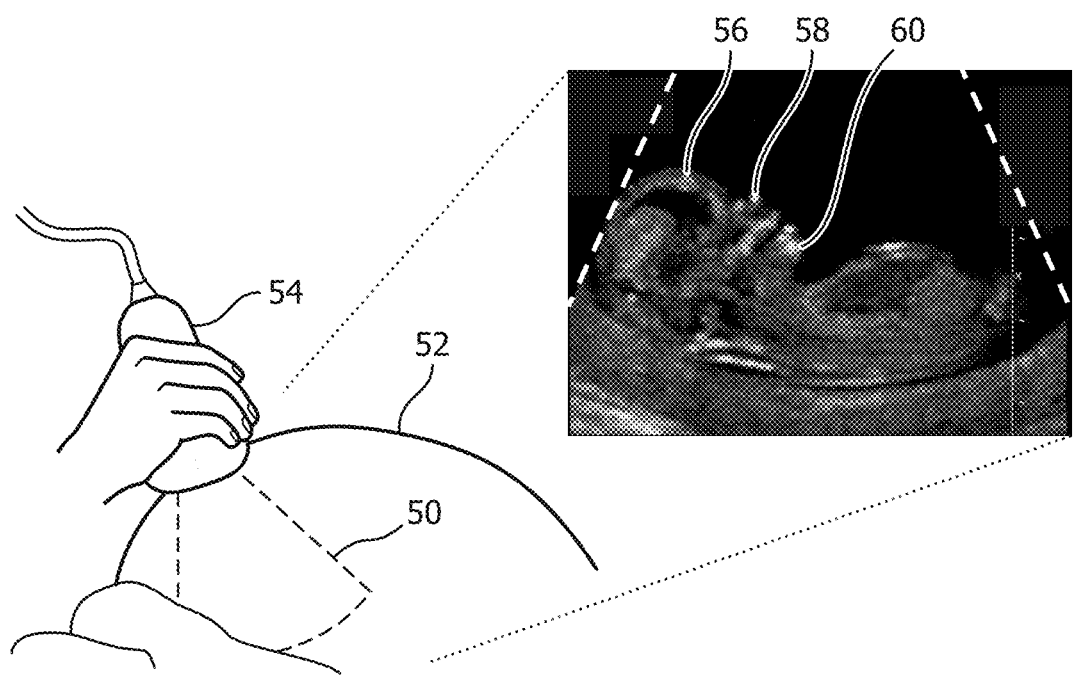
FIG. 3 depicts an example ultrasound procedure for identifying anatomical features in a fetus to determine the actual orientation of the fetus in a mother's womb.

Other features may also be detected and used to determine actual orientation. For example, the face and other landmarks can be detected. As shown in FIG. 3, an ultrasound image plane 50 corresponding to the sagittal plane can be acquired by traditional scanning of the mother 52 with an ultrasound probe 54. The forehead 56, the nose 58 and the chin 60 of the fetus can be identified using, e.g., learning-based algorithms or other models. In some embodiments, other structures such as the hypothalamus, the nasal bone end, the palatine bones, and/or the cheekbone can be identified and used to determine the fetal orientation. Upon identification of the relative positions of the various anatomical features of the fetus, the actual orientation of the fetus can be determined and, in some embodiments, displayed to the user. With respect to a fetal face, for example, the present invention further includes automated sculpting away of ultrasound data representing tissue that is not part of the facial tissue. This can be accomplished by different techniques, such as by application of the same structural model that can be applied to orient the fetal head.

As provided herein, the present invention in-part provides a quick and easy technique to display anatomical features at a desired orientation without time-consuming interaction by the sonographer during a scan. For example, instead of displaying the image of an anatomical feature in the actual orientation with respect to the probe, Step 46 of the workflow 40 includes displaying the 3D ultrasound data including the anatomical feature at a selected orientation that is different than the actual orientation. For example, a sonographer may image a fetus such that the fetus's face is actually oriented directly looking at the transducer probe. However, for better viewing of features of the fetus's face the sonographer may desire that the image be displayed at a different selected orientation in which the fetus's face is at an angle to the transducer probe. Moreover, as shown in Step 48, a lighting model can be used to add shadowing and/or lighting aspects to the 3D rendered ultrasound data displayed to the sonographer. In some embodiments, the lighting model can include one or more lights that are positioned in 3D space with respect to the rendered 3D volume of the anatomical feature, e.g., the fetus. The lights in the lighting model can be manually positioned by the user or they can be included in a standard set of positions that provide the optimal lighting and shadowing for a particular orientation of the 3D rendered ultrasound volume. In certain embodiments, relative intensities of the lighting and shadowing can be tuned by the user after displaying the 3D ultrasound image data. Furthermore, the selected orientation of the anatomical features as well as the lighting models can be saved on the system for later use and reference.

As described herein, the present invention includes displaying 3D ultrasound image data as a rendering that includes an anatomical feature of interest. In certain embodiments, the anatomical feature is positioned in a selected orientation that is different than the actual orientation, e.g. by the volume rendering and lighting model processor in FIG. 1. The anatomical feature can also be positioned in spatial relation to a lighting model such that lighting and shadowing regions on the anatomical feature are displayed according to a stored setting on an ultrasound system. In some embodiments, the stored setting for the positioning and lighting model details can be generated by a user selecting the selected orientation from a plurality of displayed orientation views. In addition, the stored setting can be configured to be used for a plurality of sequential ultrasound scans. For instance, the same selected orientation can be used for sequential patient scans such that each baby face ultrasound image has the same orientation and same lighting model for different patients. This aspect can improve throughput, for example, with scanning procedures such that a sonographer does not have to spend time orienting the rendering and lighting. Instead, the system of the present invention has a stored setting, which can be selected by a user, that initiates these steps automatically.

Figure 4:
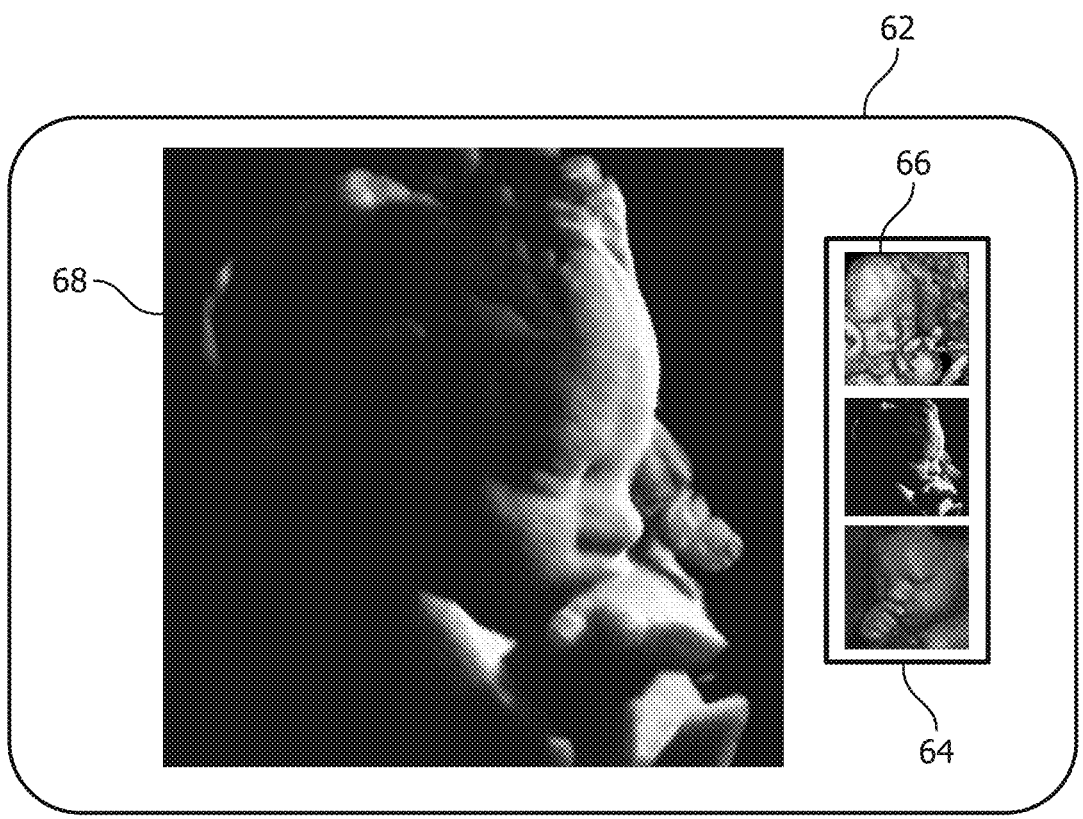
FIG. 4 illustrates a display of different selected orientations of anatomical features that can be stored on an ultrasound system for quick and reproducible viewing by a user.

FIG. 4 illustrates an embodiment of the present invention in which an ultrasound system includes three stored settings that show selected orientations of the baby's face rendered in 3D and having different lighting models to highlight certain features of the baby's face. The display 62, for example, includes three thumbnail images 64 that show real-time renderings of the 3D ultrasound image data acquired of a baby's face. Each of the selected orientations 66 of the baby's face can be displayed to a user and the user can select the desired orientation among the three. After selection, e.g., using a touchscreen input, mouse or other input device, the selected orientation of interest can be displayed in a fuller view 68 to the user. The image of the baby's face can be simply saved and printed or provided electronically to a mother. The stored settings on the system may be provided by default on an ultrasound system. Alternatively, a sonographer or other clinician can manually define the selected orientations and store those settings on the system for later use, e.g., as shown in FIG. 4. It is noted that the present invention can also be applied for viewing other tissue structures in a fetus, such as a hand or foot. In another example, a heart could be imaged similar to the fetus as described herein. A heart model could be used to identify the orientation of the heart, and a selected orientation could be used to show the heart at a different orientation than the actual orientation shown in the acquired 3D ultrasound data. The selected orientations could be designed such that a specific chamber of the heart is always displayed in a certain orientation, and in addition with lighting and shadowing to better view specific tissue areas of the heart for better diagnostic capabilities.

It will be understood that the examples and embodiments described herein are for illustrative purposes and that various modifications or changes in light thereof may be suggested to persons skilled in the art and are included within the spirit and purview of this application and scope of the appended claims. Moreover, different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A method for displaying a 3D ultrasound image in a desired view orientation, the method comprising:
    acquiring 3D ultrasound image data comprising a view of an anatomical feature in a patient, wherein the anatomical feature comprises at least a portion of a heart;
    determining an actual orientation of the anatomical feature in relation to a transducer probe, wherein determining the actual orientation comprises applying a heart model to define a surface orientation of the anatomical feature, identifying anatomical landmarks in the anatomical feature, or a combination thereof; and
    displaying, at the same time and based on the acquired image data comprising the view of the anatomical feature, a plurality of real-time volume renderings of the 3D ultrasound image data, each real-time volume rendering being selectable by a user for displaying an enhanced view, wherein each of the plurality of real-time volume renderings comprises the anatomical feature as perceived from a different orientation than the acquired image data comprising the view of the anatomical feature and wherein each of the plurality of volume renderings is in spatial relation to a different lighting model such that lighting and shadowing regions on the anatomical feature are displayed.

2. The method of claim 1, wherein the lighting and shadowing regions on the anatomical feature are displayed according to stored settings associated with the different lighting models on an ultrasound system.

3. The method of claim 2, wherein the stored settings are generated by a user selecting the different orientation of each of the plurality of real-time volume renderings.

4. The method of claim 2, wherein the stored settings are configured to be used for a plurality of sequential ultrasound scans of different patients.

5. The method of claim 2, wherein the stored settings are selected by a user.

6. The method of claim 1, wherein relative intensities of the lighting and shadowing can be tuned by the user in one or more of the plurality of real-time volume renderings after displaying the 3D ultrasound image data.

7. The method of claim 6, further comprising saving each of the different orientations of the 3D ultrasound image on the ultrasound system.

8. The method of claim 1, wherein the at least a portion of the heart comprises a specific chamber of the heart.

9. The method of claim 1, wherein each of the plurality of real-time volume renderings are displayed as a thumbnail image prior to a user selection thereof.

10. A system for displaying a 3D ultrasound image volume in a desired view orientation, the system comprising
    a transducer probe configured to acquire 3D ultrasound image data comprising an anatomical feature in a patient, wherein the anatomical feature comprises at least a portion of a heart;
    a processor to determine an actual orientation of the anatomical feature in space, wherein determining the actual orientation comprises applying a heart model to define a surface orientation of the anatomical feature, identifying anatomical landmarks in the anatomical feature, or a combination thereof; and
    a display configured to display, at the same time and based on the acquired image data comprising the view of the anatomical feature, a plurality of real-time volume renderings of the 3D ultrasound image data, each real-time volume rendering being selectable by a user for displaying an enhanced view, wherein each of the plurality of real-time volume renderings comprises the anatomical feature as perceived from a different orientation than the acquired image data comprising the view of the anatomical feature and wherein each of the plurality of real-time volume renderings is in spatial relation to a different lighting model such that lighting and shadowing regions on the anatomical feature are displayed.

11. The system of claim 10, wherein the lighting and shadowing regions on the anatomical feature are displayed according to stored settings associated with the different lighting models on an ultrasound system.

12. The system of claim 10, wherein the display is configured to display each real-time volume rendering according to a user selection of a setting.

13. The system of claim 10, wherein the different orientation of each real-time volume rendering is pre-selected before the acquiring of the 3D ultrasound image data.

14. The system of claim 10, wherein the system is further configured to select a lighting model from the different lighting models to provide shading and lighting of a rendering of the 3D ultrasound image data.

15. The system of claim 10, wherein the at least a portion of the heart comprises a specific chamber of the heart.

16. The system of claim 10, wherein each of the plurality of real-time volume renderings are displayed as a thumbnail image prior to a user selection thereof.

17. The system of claim 10, wherein the system is further configured to tune, in response to a user instruction, relative intensities of the lighting and shadowing in one or more of the plurality of real-time volume renderings.

* * * * *